United States Patent
Lee

(10) Patent No.: US 12,080,181 B2
(45) Date of Patent: Sep. 3, 2024

(54) ORAL CARE METHOD USING ELECTRIC TOOTHBRUSH WHICH IS CAPABLE OF BEING INTERLINKED WITH APPLICATION

(71) Applicant: BLUEREO INC., Seoul (KR)

(72) Inventor: Seung Min Lee, Seoul (KR)

(73) Assignee: BLUEREO INC., Seoul (KR)

( * ) Notice: Subject to any disclaimer, the term of this patent is extended or adjusted under 35 U.S.C. 154(b) by 913 days.

(21) Appl. No.: 16/977,764

(22) PCT Filed: Jul. 27, 2020

(86) PCT No.: PCT/KR2020/095092
§ 371 (c)(1),
(2) Date: Sep. 2, 2020

(87) PCT Pub. No.: WO2021/091362
PCT Pub. Date: May 14, 2021

(65) Prior Publication Data
US 2022/0151754 A1    May 19, 2022

(30) Foreign Application Priority Data

Nov. 7, 2019  (KR) .................. 10-2019-0142004
Dec. 30, 2019 (KR) .................. 10-2019-0178593

(51) Int. Cl.
| | | |
|---|---|---|
| G09B 19/00 | (2006.01) | |
| A61C 17/22 | (2006.01) | |
| A61C 17/34 | (2006.01) | |
| G16H 20/40 | (2018.01) | |
| A46B 15/00 | (2006.01) | |

(52) U.S. Cl.
CPC ........ *G09B 19/0084* (2013.01); *A61C 17/221* (2013.01); *A61C 17/3481* (2013.01); *G16H 20/40* (2018.01); *A46B 15/0016* (2013.01)

(58) Field of Classification Search
CPC ... A61C 17/221; A61C 17/32; A61C 17/3481; A46B 15/0016; G09B 19/0084
See application file for complete search history.

(56) References Cited

U.S. PATENT DOCUMENTS 9,462,878 B1 *  10/2016  Filo ..................... A46B 15/0006
10,925,387 B2 *  2/2021  Nishiura .................. A46B 5/00
(Continued)

FOREIGN PATENT DOCUMENTS

| EP | 0221296 A1 | 5/1987 |
| JP | 6551110 B2 | 7/2019 |

(Continued)

OTHER PUBLICATIONS

Naver Blog, "Philips Sonicare DiamondClean Smart Smart White Edition (HX9924/06)" [online], Oct. 23, 2018. Article link: https://m.blog.naver.com/snoopyjk/221382830429. Youtube link: https://www.youtube.com/watch?v=LAHPwKmOAa0&t=61s&ab_channel=snoopy.

*Primary Examiner* — Steve Rowland
(74) *Attorney, Agent, or Firm* — Bridgeway IP Law Group, PLLC; Sang Ho Lee; Hyun Woo Shin

(57) ABSTRACT

An oral care method using an electric toothbrush includes receiving brushing data from an electric toothbrush, by an application; and analyzing the brushing data by the application to display a brushing score indicating how much the brushing is performed.

8 Claims, 23 Drawing Sheets

(56) References Cited

U.S. PATENT DOCUMENTS

| | | | | |
|---|---|---|---|---|
| 2007/0270221 | A1* | 11/2007 | Park | A61C 17/00 |
| | | | | 463/37 |
| 2009/0092955 | A1* | 4/2009 | Hwang | G16H 20/40 |
| | | | | 434/263 |
| 2009/0291422 | A1* | 11/2009 | Puurunen | A46B 15/0002 |
| | | | | 434/263 |
| 2013/0125326 | A1 | 5/2013 | Schmid et al. | |
| 2016/0027327 | A1* | 1/2016 | Jacobson | G09B 19/0084 |
| | | | | 434/263 |
| 2018/0020819 | A1* | 1/2018 | Steckling | A46B 15/0044 |
| | | | | 15/167.1 |
| 2018/0098620 | A1* | 4/2018 | Lee | A61C 17/3481 |
| 2018/0192765 | A1 | 7/2018 | Jeanne et al. | |
| 2020/0134352 | A1* | 4/2020 | Choi | G06T 7/30 |
| 2020/0179089 | A1* | 6/2020 | Serval | A46B 9/04 |
| 2021/0085439 | A1* | 3/2021 | Fishman | A61C 17/20 |
| 2021/0153989 | A1* | 5/2021 | Huang | A46B 15/0006 |
| 2021/0177558 | A1* | 6/2021 | Payne | A46B 15/0002 |
| 2021/0201687 | A1* | 7/2021 | Choi | G16H 40/60 |
| 2021/0289271 | A1* | 9/2021 | Huang | A46B 15/0006 |
| 2021/0361060 | A1* | 11/2021 | Huang | A46B 15/0038 |
| 2022/0249214 | A1* | 8/2022 | Serval | G16H 40/63 |

FOREIGN PATENT DOCUMENTS

| | | |
|---|---|---|
| KR | 10-1021330 B1 | 3/2011 |
| KR | 10-1438819 B1 | 9/2014 |
| KR | 10-2017-0022003 A | 3/2017 |
| KR | 10-2018-0040060 A | 4/2018 |
| KR | 10-2018-0116859 A | 10/2018 |
| KR | 10-2019-0114183 A | 10/2019 |

* cited by examiner

FIG.6C

ORAL CARE METHOD USING ELECTRIC TOOTHBRUSH WHICH IS CAPABLE OF BEING INTERLINKED WITH APPLICATION

TECHNICAL FIELD

The present invention relates to an oral care method using an electric toothbrush, and more particularly, to an oral care method using an electric toothbrush which is capable of being interlinked with an application.

BACKGROUND ART

The most common tool for cleaning teeth is a toothbrush which is used to brush the teeth with toothpaste for teeth health care and hygiene. The toothbrush includes a main body in the form of a stick and a brush in which thin hair members are densely implanted in a washing body formed at one end of the main body.

Generally, when a user uses the toothbrush, if the user brushes the teeth using the movement of the wrist or arm, it is uncomfortable because force is applied to the wrist or arm. Further, a force which moves the toothbrush is often inconsistent, which causes an injury to the gums or mouth.

Therefore, a mechanical device has been developed to reduce a variation in the effect of removing bacteria according to individual hand skills and allow the user to easily brush the teeth without requiring much force and the mechanical device is an electric toothbrush.

Generally, there are two operating methods of an electric toothbrush: A vibrating and rotating electric toothbrush which vibrates and rotates a brush head using a motor and a sonic electric toothbrush which generates a strong flow of water using a motor to brush the teeth.

However, there is a disadvantage in that it is difficult to systematically manage the oral care using the existing electric toothbrush which simply cleans the teeth using the electric toothbrush. Therefore, a demand for a system which is interlinked with the electric toothbrush to systematically manage the oral care is gradually increasing.

DISCLOSURE

Technical Problem

An embodiment of the present invention provides an oral care method using an electric toothbrush which is capable of being interlinked with an application which registers users for individual electric toothbrushes and analyzes and evaluates data in accordance with brushing actions of the users to manage the oral care.

Technical objects of the present disclosure are not limited to the aforementioned technical objects and other technical objects which are not mentioned will be apparently appreciated by those skilled in the art from the following description.

Technical Solution

An oral care method using an electric toothbrush according to an embodiment of the present invention includes receiving brushing data from an electric toothbrush, by an application; and display a brushing score indicating how much the brushing is performed, by the application, by analyzing the brushing data.

Desirably, the displaying of a brushing score includes calculating the brushing score by the following Equation:

$$\text{Brushing score} = \text{Number of brushing times} * A + \text{Brushing hour (s)} * B - \text{Point of brushing strength} \quad [\text{Equation}]$$

(A and B are constants and a score of the brushing strength is a value obtained by converting a pressure when the brushing is performed into a predetermined value)

Desirably, the receiving of brushing data includes receiving on-time and off-time data from the electric toothbrush and calculating a difference therebetween into a brushing hour.

Desirably, the displaying of a brushing score includes displaying values obtained by cumulatively adding the brushing scores on a daily basis together with daily statistic data for each day on a weekly basis.

Desirably, the displaying of a brushing score includes displaying values obtained by cumulatively adding the brushing scores on a daily basis together with data obtained by visualizing the brushing score for each day on a monthly basis.

Desirably, the oral care method may further include sharing the brushing score with an application of the other device.

Desirably, the oral care method may further include receiving an input regarding a setting of the electric toothbrush from a user, by the application; and transmitting a control signal of the electric toothbrush in accordance with the input to the electric toothbrush, by the application.

Desirably, the oral care method may further include: receiving a current consumption measurement value of a vibrating motor from the electric toothbrush, by the application; and determining a brushing strength by comparing the current consumption measurement value with a predetermined optimal current value, by the application.

Desirably, the receiving of brushing data includes: receiving the brushing data in real time and the displaying of a brushing score includes: analyzing a direction of a brush head of the electric toothbrush and a direction of a reciprocating motion for brushing to determine a tooth which is being brushed and a progressive degree of the brushing and displaying the determined result to the user in real time.

Advantageous Effects

The effect according to the present invention is as follows:

According to the embodiment of the present invention, the users are registered for individual electric toothbrushes using an application to analyze and evaluate data in accordance with the brushing actions of the users, thereby systematically managing the oral care.

DESCRIPTION OF DRAWINGS

FIGS. 6A to 6D are views illustrating a user screen (GUI) of a brushing data sharing function of an application which is capable of being interlinked with an electric toothbrush according to an embodiment of the present invention.

BEST MODE

Figure 1:
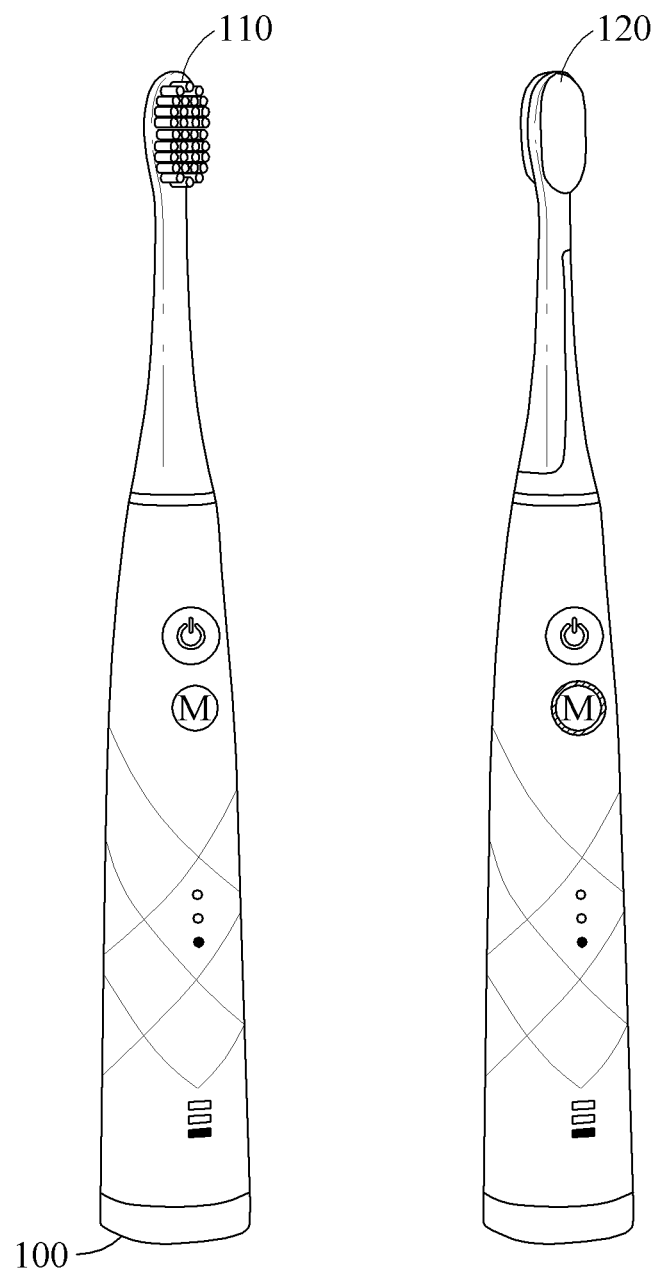
FIGS. 1 and 2 are views for explaining a structure of an electric toothbrush according to an embodiment of the present invention.

Those skilled in the art may make various modifications to the present invention and the present invention may have various embodiments thereof, and thus specific embodiments will be described in detail with reference to the drawings. However, it should be understood that the present invention is not limited to the specific embodiments, but includes all changes, equivalents, or alternatives which are included in the spirit and technical scope of the present invention. In the description of respective drawings, similar reference numerals designate similar elements.

Terms such as first, second, A, or B may be used to describe various components, but the components are not limited by the above terms. The above terms are used only to discriminate one component from the other component. For example, without departing from the scope of the present invention, a first component may be referred to as a second component, and similarly, a second component may be referred to as a first component. A term of "and/or" includes combination of a plurality of related elements or any one of the plurality of related elements.

It should be understood that, when it is described that an element is "coupled" or "connected" to another element, the element may be directly coupled or directly connected to the other element or coupled or connected to the other element through a third element. In contrast, when it is described that an element is "directly coupled" or "directly connected" to another element, it should be understood that no element is not present therebetween.

Terms used in the present application are used only to describe a specific exemplary embodiment, but are not intended to limit the present invention. A singular form may include a plural form if there is no clearly opposite meaning in the context. In the present application, it should be understood that term "include" or "have" indicates that a feature, a number, a step, an operation, a component, a part or the combination those of described in the specification is present, but do not exclude a possibility of presence or addition of one or more other features, numbers, steps, operations, components, parts or combinations, in advance.

If it is not contrarily defined, all terms used herein including technological or scientific terms have the same meaning as those generally understood by a person with ordinary skill in the art. Terms defined in generally used dictionary shall be construed that they have meanings matching those in the context of a related art, and shall not be construed in ideal or excessively formal meanings unless they are clearly defined in the present application.

In the specification and the claim, unless explicitly described to the contrary, the word "comprise" and variations such as "comprises" or "comprising", will be understood to imply the inclusion of stated elements but not the exclusion of any other elements.

Hereinafter, exemplary embodiments according to the present invention will be described in detail with reference to accompanying drawings.

Figure 2:
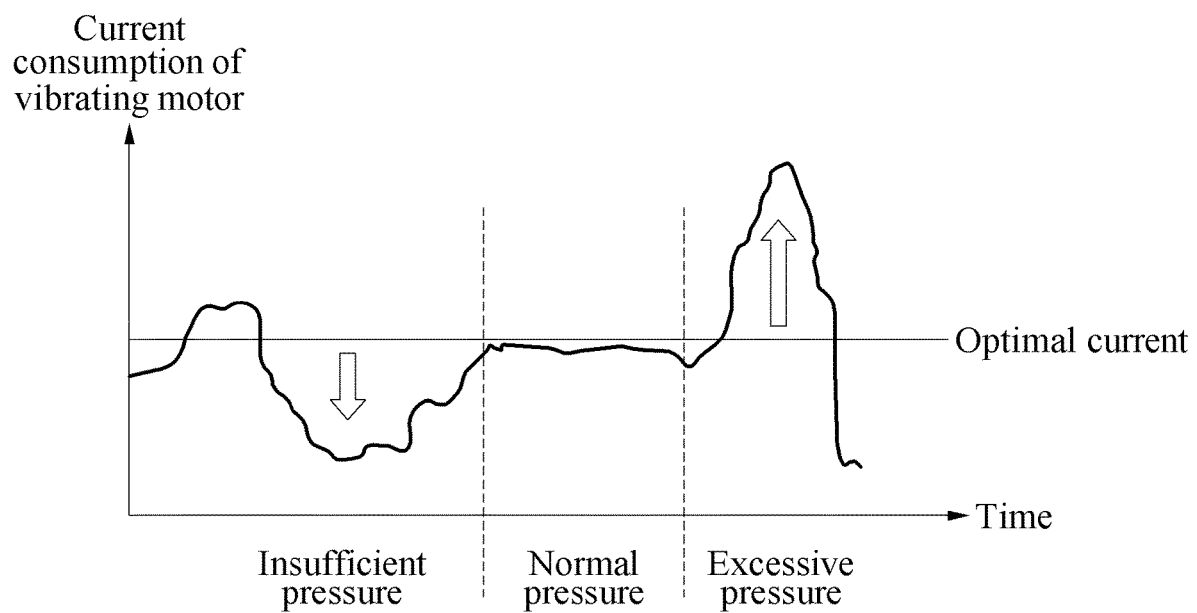

FIGS. 1 and 2 are views for explaining a structure of an electric toothbrush according to an embodiment of the present invention.

Referring to FIG. 1, an example that a brush head 110 is coupled to a head part of an electric toothbrush 100 and an example that a massage tip 120 is coupled to the head part are illustrated. The brush head 110 and the massage tip 120 are provided to be exchangeable. Further, both the brush head 110 and the massage tip 120 receive the vibration from a main body to transmit the vibration to teeth and gums.

For example, the electric toothbrush 100 of the present invention may include a heating element. When the massage tip 120 is used, if the heating element is operated, heat is generated from the heating element in the massage tip 120 so that a smooth heat feeling may be transmitted to the gums. Further, the heating element and the vibrating function may be simultaneously used. Further, the massage tip 120 of FIG. 1 is configured with a soft silicon material to enhance the feeling of use. Further, the massage tip is manufactured to have a streamlined shape to enhance the massage effect for a contact area of the gums.

For example, the electric toothbrush 100 of the present invention may include a Bluetooth communication module. Alternatively, the electric toothbrush 100 further includes a wireless communication module such as LTE or Wi-Fi as well as the Bluetooth. In addition, the electric toothbrush 100 may include a 6-axis sensor. Rotation, a gradient, and a speed of the electric toothbrush 100 may be sensed using the 6-axis sensor. Information about the movement of the electric toothbrush 100 collected as described above may be transmitted to an application of a smartphone by means of the wireless communication module such as the Bluetooth described above.

For example, the collected data is processed to recognize the motion during the brushing. For example, it is possible to distinguish an operation of brushing a lower molar, an operation of brushing a front tooth, or an operation of brushing an upper molar. To this end, information indicating whether a user of the electric toothbrush 100 is a right-handed person or a left-handed person may be additionally input. When the motion data is analyzed as described above, a diagram indicating whether the user of the electric toothbrush 100 evenly brushes the teeth may be provided through the application.

For example, the electric toothbrush 100 of the present invention may include a mode change button. The mode change button may adjust a vibrating speed of the vibrating motor of the main body. For example, a vibration mode including three levels of strong, medium, and weak may be provided.

For example, the electric toothbrush 100 of the present invention may include a sensor unit which senses a pressure. For example, when a strong pressure is applied to the brush head 110 or the massage tip 120, the load of the vibrating motor is increased so that current consumption of the vibrating motor varies. It is determined whether the pressure is insufficient, normal, or excessive by measuring the current consumption in accordance with the vibration of the vibrating motor.

Referring to FIG. 2, a measurement value of the current consumption of the vibrating motor in accordance with the change of time is illustrated. In this case, an optimal current reference value of a mode in which the electric toothbrush 100 operates and the measured current consumption are compared to determine the overload of the pressure. For example, when the measured current consumption value is lower than the optimal current reference value, a pressure applied to the brush head 110 is not sufficient. In contrast, when the measured current consumption value is higher than the optimal current reference value, a higher pressure has been applied to the brush head 110.

As illustrated in FIG. 2, there is a predetermined reference value of an optimal current for every mode and it is determined whether the pressure is insufficient/optimal/excessive based on the reference value. In this case, in order to more precisely measure a pressure, when the current consumption is out of from the reference value of the optimal current by a predetermined % or more or a predetermined time or longer, it is determined that the pressure is excessive/optimal/insufficient.

Figure 3A:
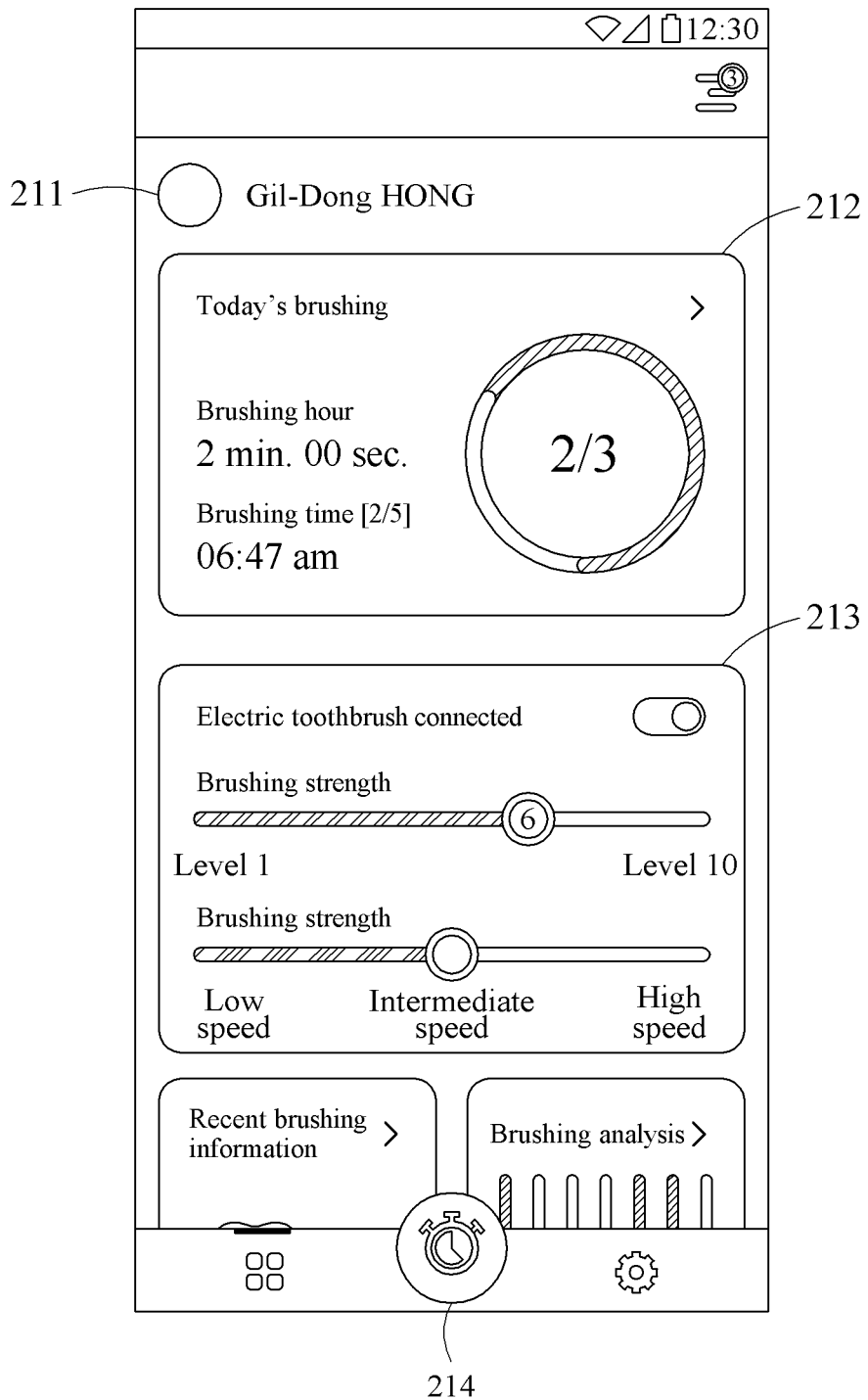
FIGS. 3A to 3C are views illustrating a user screen (GUI) of a basic function of an application which is capable of being interlinked with an electric toothbrush according to an embodiment of the present invention.
Figure 3B:
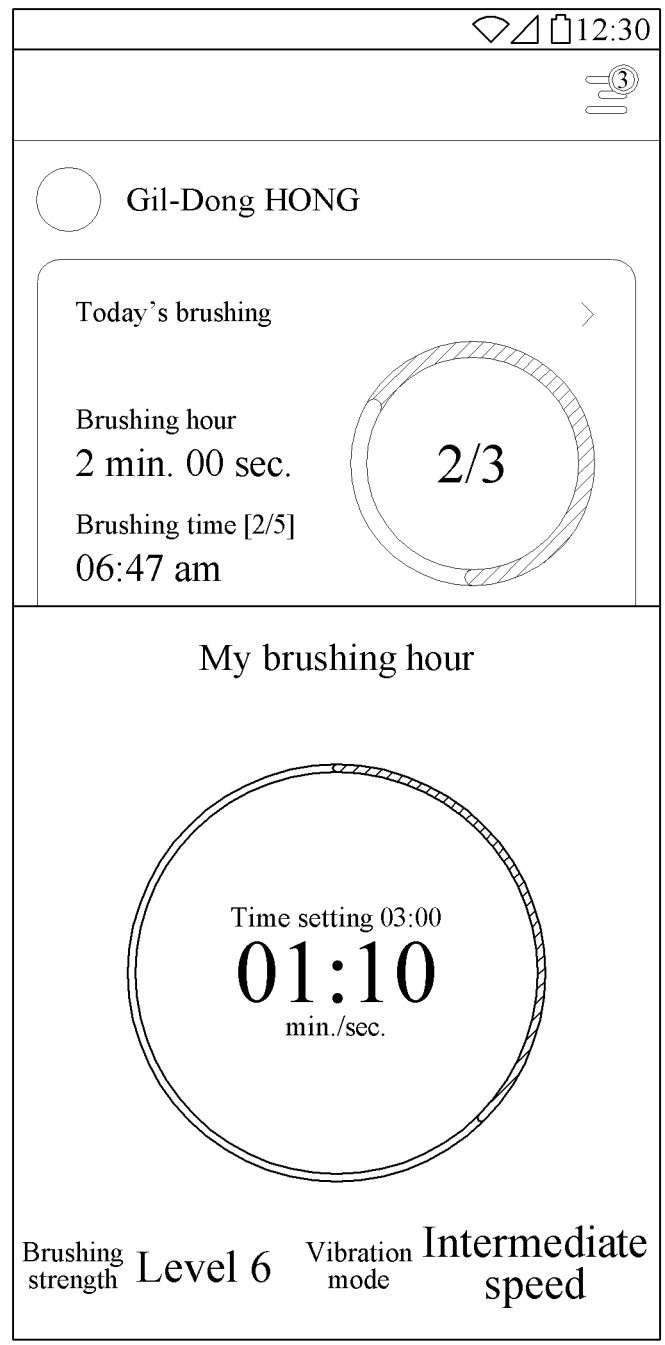
Figure 3C:
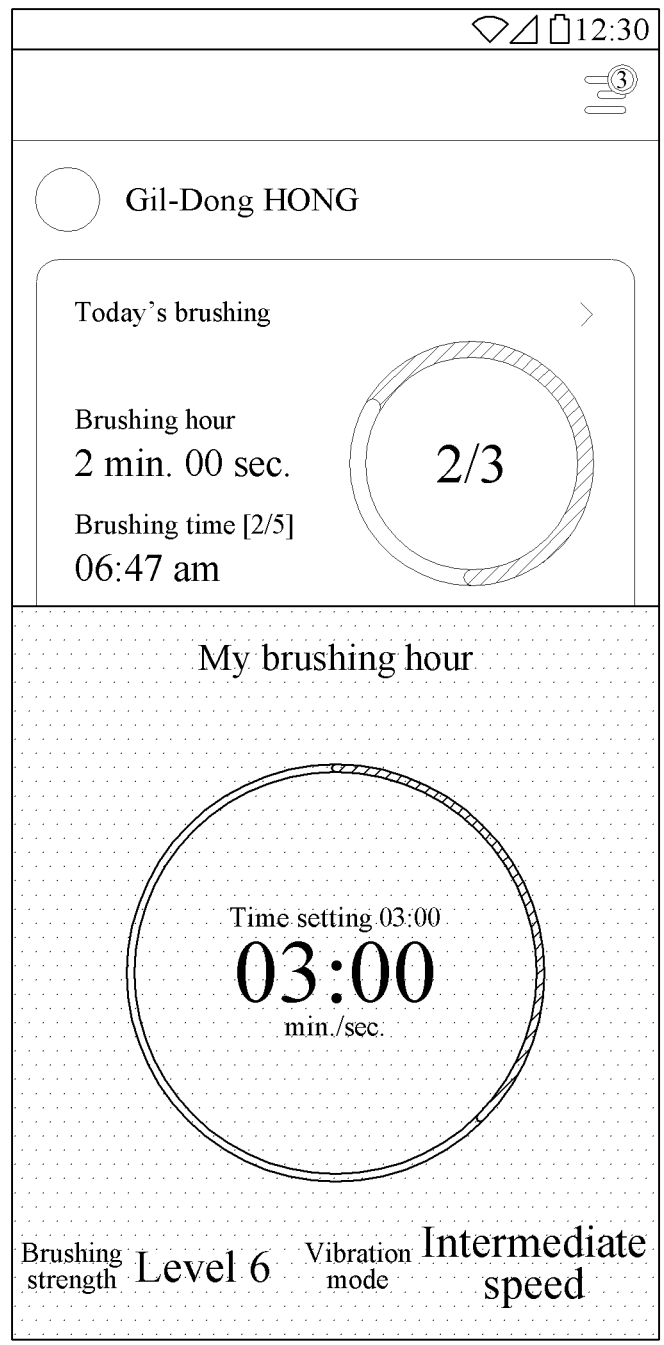

FIGS. 3A to 3C are views illustrating a user screen (GUI) of a basic function of an application which is capable of being interlinked with an electric toothbrush according to an embodiment of the present invention.

Referring to FIG. 3A, it is understood that a user of the electric toothbrush 100 has been registered in an application through a user information area 211 in an upper portion of the application. As described above, the oral care system proposed by the present invention is used to register a user for every electric toothbrush and manage data for every user.

For example, when the electric toothbrush 100 is interlinked with the smartphone, a code assigned to every electric toothbrush is generated to recognize individual users. Further, data may be transmitted and received between the electric toothbrush 100 and a smartphone application through a wireless communication module such as Bluetooth.

For example, data regarding the number of brushing times on a specific date, a cumulative brushing hour, and a time when the user brushes the teeth may be checked through a Today's brushing information area 212. Referring to FIG. 3A, it is understood that the user brushed teeth for a total of two minutes and the number of brushing times was a total of two times from an indicator displayed as 2/3. If the user brushes the teeth one more time, the indicator is changed to 3/3. Here, 3 which is the denominator means the number of times that the user has set to brush the teeth in advance. Referring to FIG. 3A, it is confirmed that the last brushing time was 6:47 am.

For example, a setting of the electric toothbrush 100 may be allowed through an electric toothbrush connection area 213. That is, not only information regarding the brushing is received by being interlinked with the Bluetooth, but also a brushing strength of the electric toothbrush 100, a vibration mode, and a vibrating speed are set.

For example, on/off data of a vibrating function of the electric toothbrush 100 is interlinked to automatically record the brushing hour through a brushing timer area 214. Alternatively, when there is no interlinkable electric toothbrush 100, the timer is manually operated to record the brushing hour.

Referring to FIG. 3B, the electric toothbrush 100 and the smartphone are connected through the Bluetooth and a screen which automatically measures the brushing hour may be seen. It is possible to measure a used brushing strength, a current vibration mode, and a current brushing hour, in real time. That is, as soon as the vibration mode of the electric toothbrush 100 is on/off, the brushing timer is automatically activated to start/stop.

In contrast, referring to FIG. 3C, a screen which manually turns on/off a timer function in a state when the electric toothbrush 100 and the smartphone are not connected can be seen. In this case, the user may also manually input the brushing strength or the vibration mode. As described above, even in a situation when the electric toothbrush 100 cannot be interlinked, information regarding the brushing is input manually, to systematically manage the oral care.

Figure 4A:
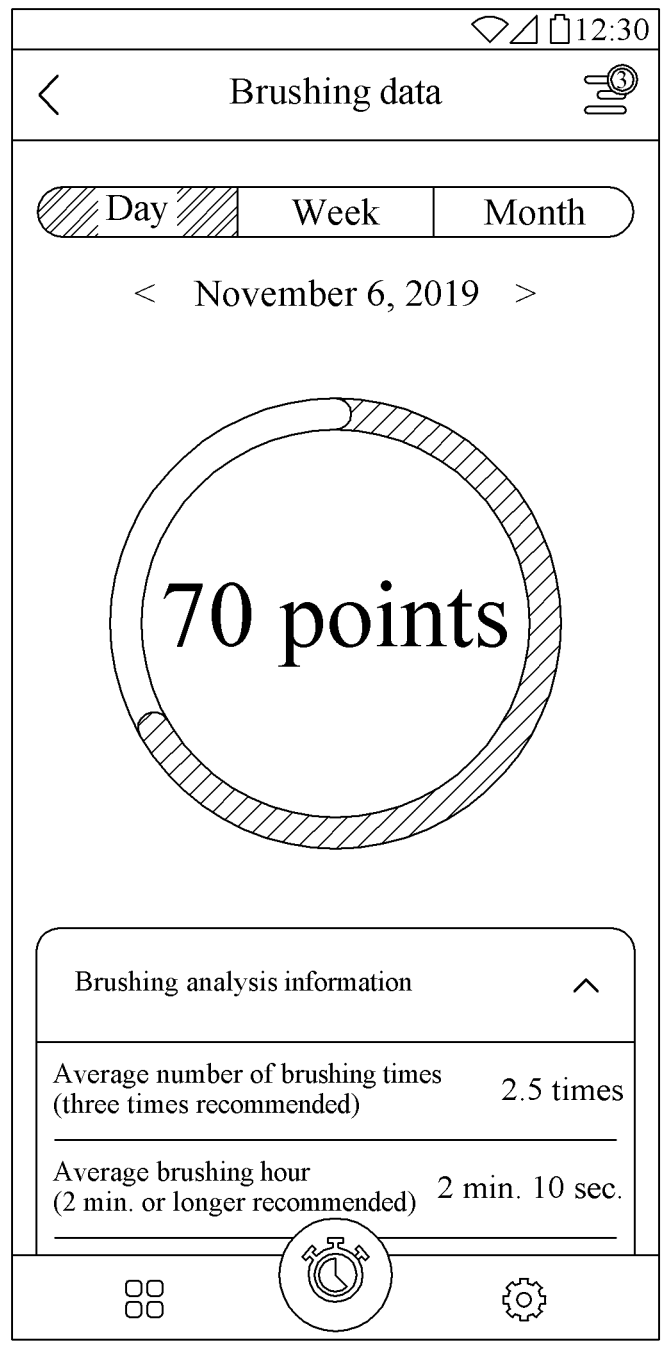
FIGS. 4A to 4C are views illustrating a user screen (GUI) of a brushing data checking function of an application which is capable of being interlinked with an electric toothbrush according to an embodiment of the present invention.
Figure 4B:
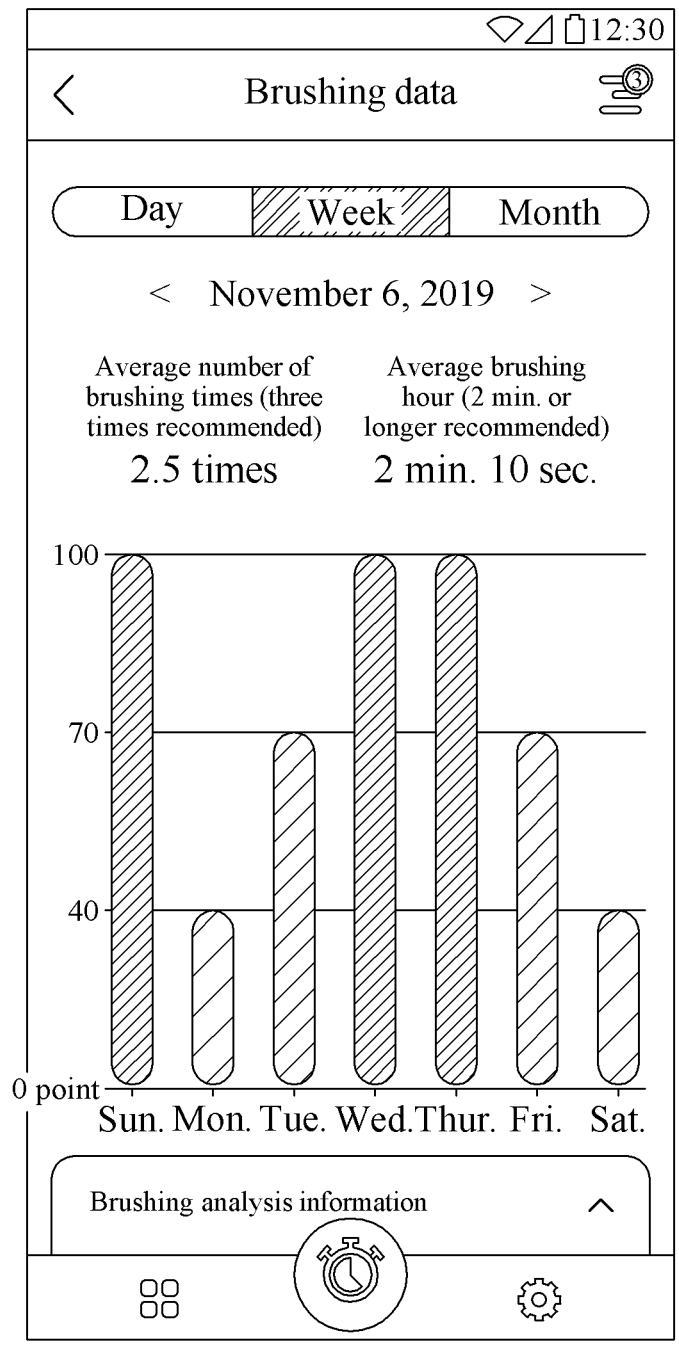
Figure 4C:
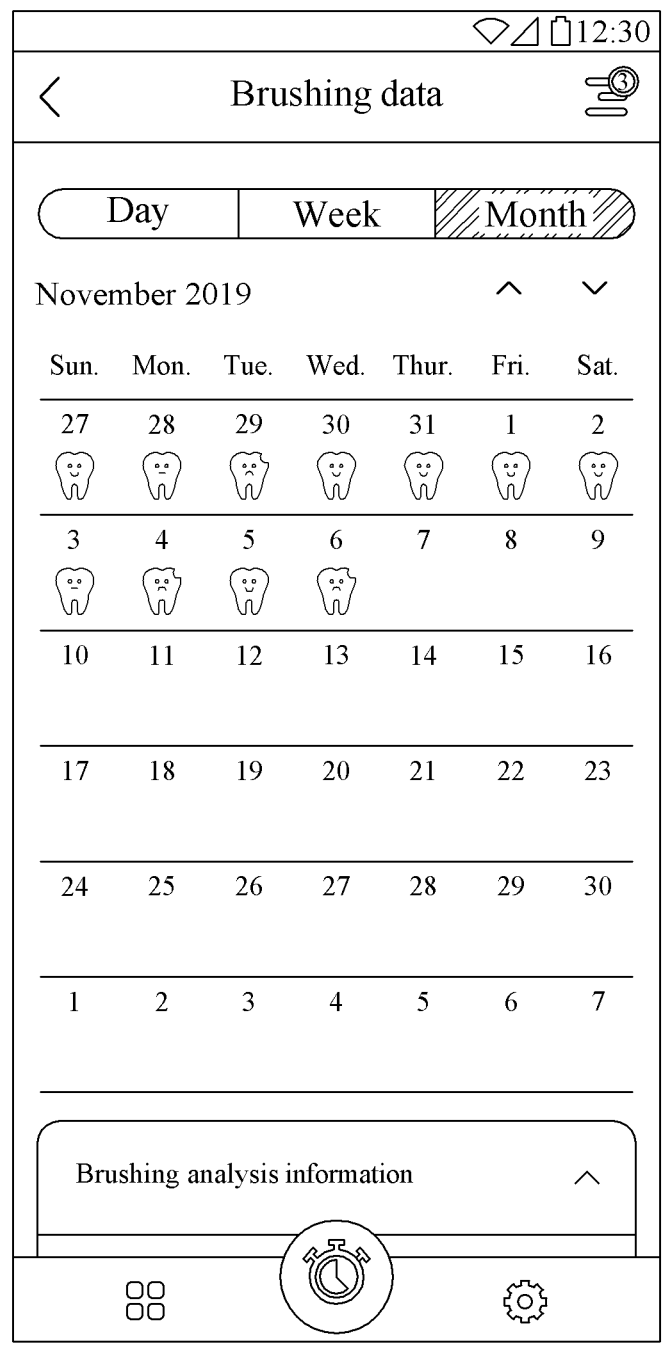

FIGS. 4A to 4C are views illustrating a user screen (GUI) of a brushing data checking function of an application which is capable of being interlinked with an electric toothbrush according to an embodiment of the present invention.

Referring to FIG. 4A, the brushing record may be checked on a daily basis, referring to FIG. 4B, the brushing record may be checked on a weekly basis, and referring to FIG. 4C, the brushing record may be checked on a monthly basis.

Referring to FIG. 4A, brushing data on Nov. 6, 2019 may be checked. The brushing on the corresponding date is scored as 70 points to be intuitively notified to the user. According to an embodiment, the brushing score is calculated by the following Equation.

$$\text{Brushing score} = \text{Number of brushing times} * 18 \text{ points} + \text{Brushing hour (seconds)} * 0.1 \text{ point} - \text{Score of brushing strength} \qquad \text{[Equation 1]}$$

Referring to Equation 1, 18 points for every brushing time are added. Further, 0.1 point for every second is added for the brushing hour, but the brushing hour does not exceed a maximum of 16 points per brushing. That is, the brushing for 160 seconds or longer which is 2 minutes 30 seconds or longer is calculated to be 16 points as a full score. Therefore, it is understood that a maximum score which can be obtained by one brushing was 34 points in consideration of the number of brushing times and the brushing hour.

However, 18 points which is a constant A multiplied by the number of brushing times and 0.1 point which is a constant B multiplied by the brushing time are constants exemplified to help the understanding of the invention. Therefore, other constants may be applied to calculate the brushing score. Since the brushing score is an indicator to intuitively show how faithfully brushing is performed, different values from two constants A and B may also be set.

Next, the brushing strength is considered to be reflected to the brushing score. It is understood that the brushing strength is set from level 1 to level 10 from the screen of FIG. 3A. In this case, when the brushing strength is level 1 to level 7, 0 point is reflected, when the brushing strength is level 8, 3 points are reflected, when the brushing strength is level 9, 4 points are reflected, and when the brushing strength is level 10, 5 points are deducted. The reason why the higher the brushing strength, the higher the deducted point as described above is to encourage the user to brush the teeth with an appropriate brushing strength.

The brushing scores are calculated for each of the brushing times as described above to be accumulated day by day. Arithmetically, the maximum score which can be accumulated from one time of brushing is 34 points so that if the user brushes the teeth three times in the morning/afternoon/evening, a cumulative score for one day may be 102 points. However, for the convenience of the user, a maximum brushing score which can be accumulated daily may be limited to 100 points. Further, the decimal point may be simply represented by being rounded off/up/down.

Further, when the date is changed, the brushing score is reset to be newly calculated. Referring to FIG. 4A, in addition to the brushing score, information regarding an average number of brushing times and information regarding an average brushing hour may also be checked.

When the brushing pattern of the user is calculated as a score to be provided, it is possible to intuitively check whether the user properly brushes the teeth. Further, it is possible to induce the user to have a habit of regularly brushing the teeth at a certain number of times to get a high score. Further, it is possible to induce the user to have a habit of brushing the teeth for a predetermined time or longer. Furthermore, it is possible to induce the user to have a habit of brushing the teeth with an appropriate strength.

Referring to FIG. 4B, information regarding how much the user brushes the teeth for every day on the weekly basis: Monday, Tuesday, Wednesday, Thursday, Friday, Saturday, and Sunday may be provided. An average number of brushing times of the first week of November of 2019 was 2.5 times and an average brushing hour was 2 minutes and 10 seconds. Further, it is confirmed that the brushing scores on Monday/Wednesday/Thursday were 100 points, the brushing scores on Tuesday and Friday were 70 points, and the brushing scores on Monday and Saturday were 40 points. When the brushing scores for one week is represented by a bar graph, it is possible to intuitively confirm how regularly the user brushes the teeth. Further, it is understood that the color of the bar graph is interlinked with the brushing score so that the higher the score, the darker the blue color.

Referring to FIG. 4C, the brushing scores is represented in the form of a calendar. For example, when the brushing score is 0 to 40 points, a red tooth is represented, when the brushing score is 40 to 70 points, a yellow tooth is represented, and when the brushing score is 70 to 100 points, a blue tooth is represented. However, the example of FIG. 4C is provided to help the understanding of the present invention so that the score interval or the color is diversified to represent the brushing score on the corresponding month.

Figure 5A:
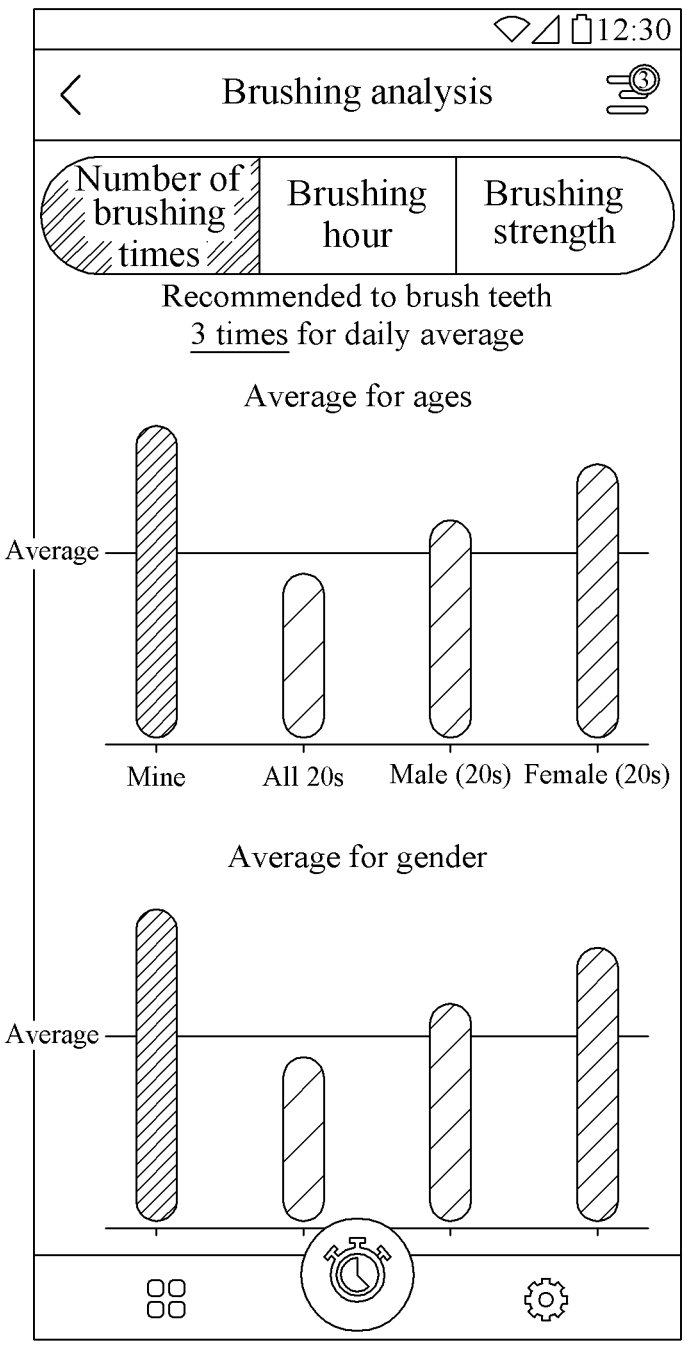
FIGS. 5A to 5C are views illustrating a user screen (GUI) of a brushing analysis function of an application which is capable of being interlinked with an electric toothbrush according to an embodiment of the present invention.
Figure 5B:
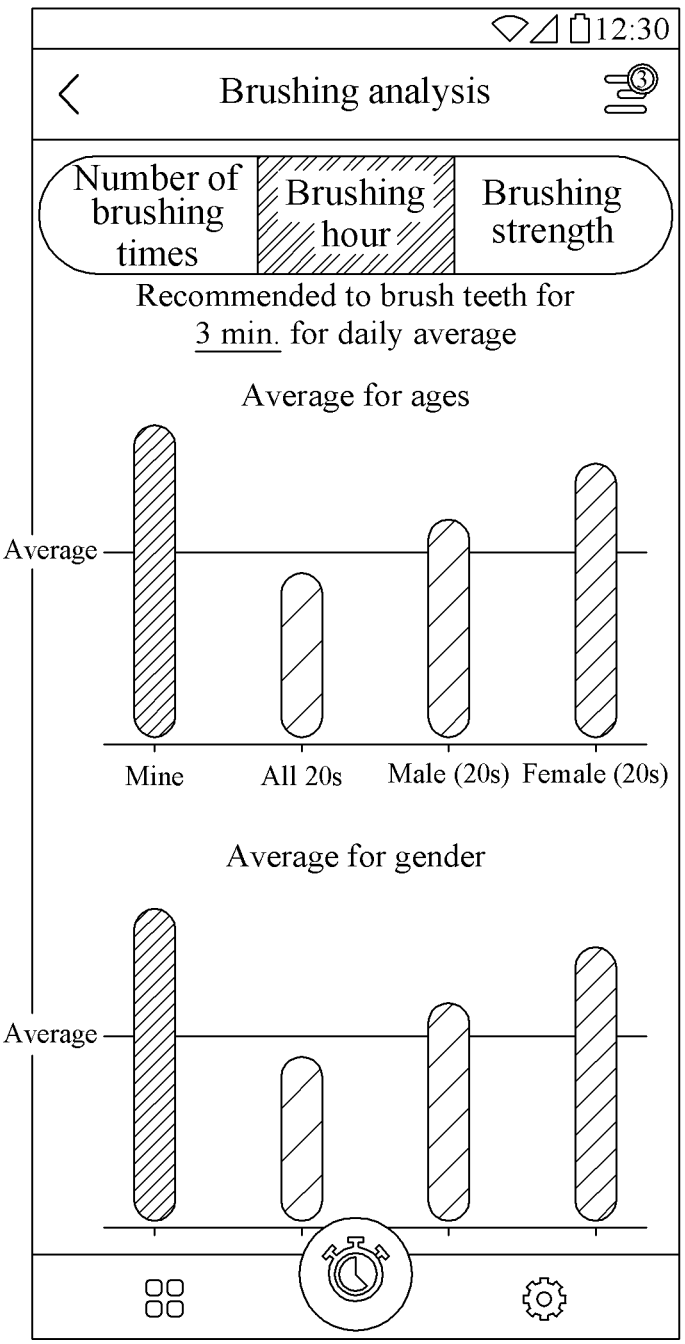
Figure 5C:
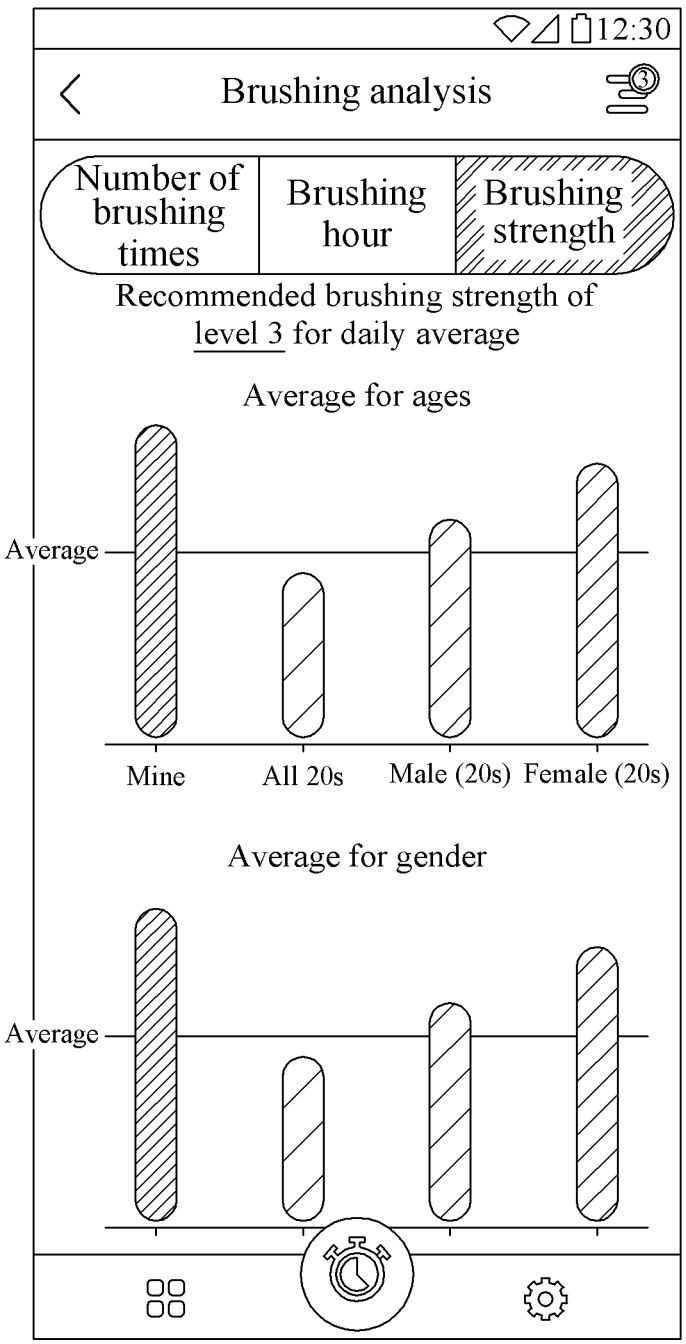

FIGS. 5A to 5C are views illustrating a user screen (GUI) of a brushing analysis function of an application which is capable of being interlinked with an electric toothbrush according to an embodiment of the present invention.

Referring to FIG. 5A, a screen which compares the average number of brushing times for ages and genders, and my score is illustrated. Referring to FIG. 5B, a screen which compares the average brushing hour for ages and genders, and my score is illustrated. Referring to FIG. 5C, a screen which compares the average brushing strength for ages and genders, and my score is illustrated. When the user's own brushing information and brushing data of the same age and the same gender are compared, there is an advantage in that the user's own brushing habit is objectively checked.

FIGS. 6A to 6D are views illustrating a user screen (GUI) of a brushing data sharing function of an application which is capable of being interlinked with an electric toothbrush according to an embodiment of the present invention.

Figure 6A:
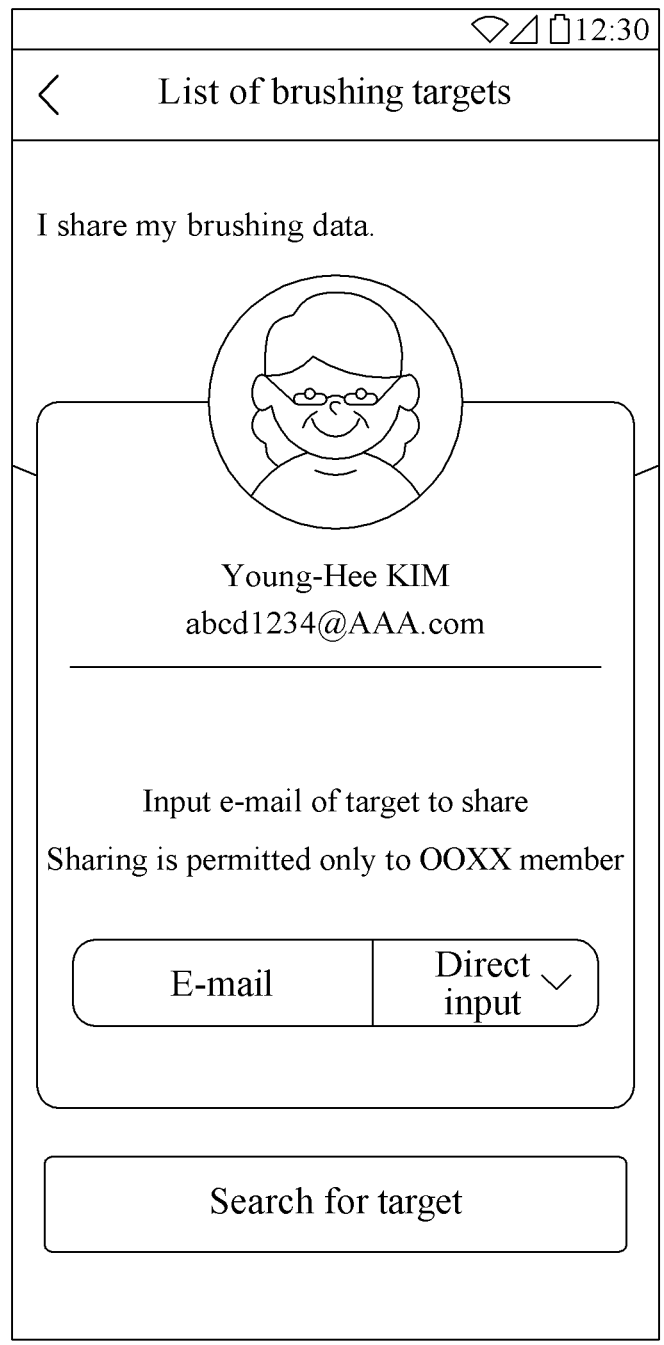

Referring to FIG. 6A, another user who shares the brushing data is registered through an e-mail. If the user applies for sharing, the brushing data stored in the user's smartphone application is shared with a third party through a server. The brushing data sharing function is provided for guardians. For example, the brushing data sharing function allows the parents to check their child's brushing data.

Figure 6B:
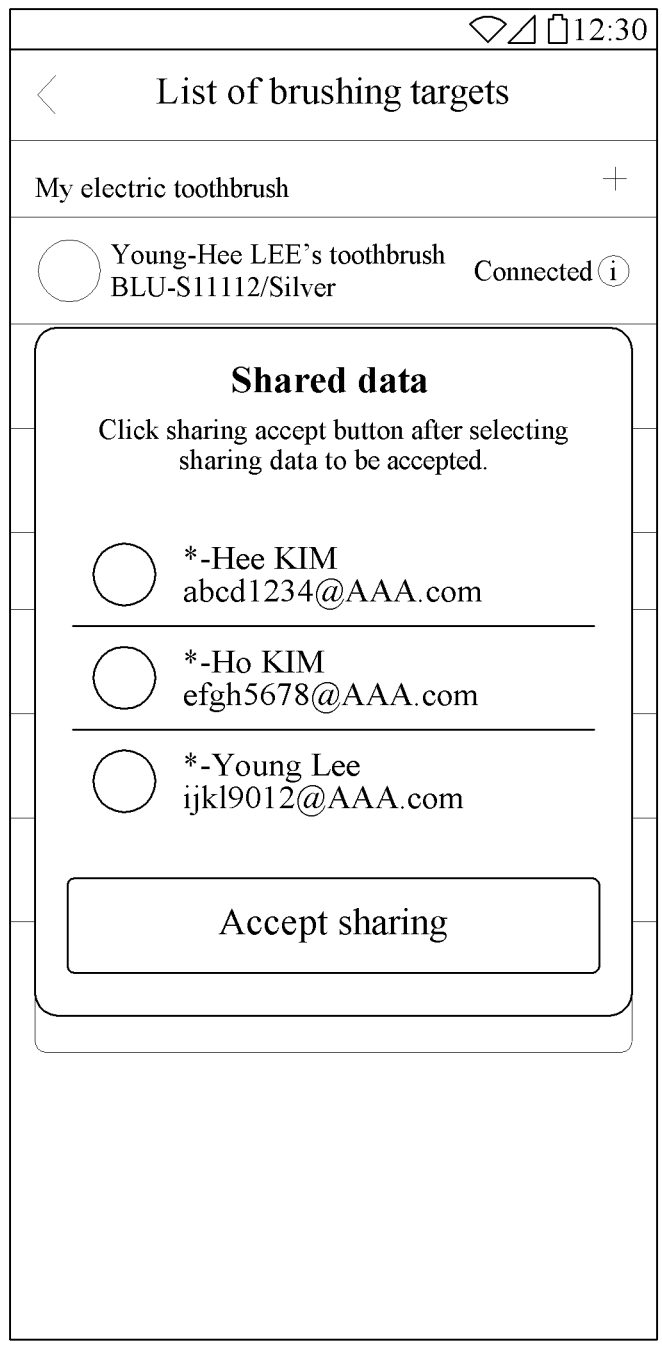

Referring to FIG. 6A, it is confirmed that a user named Chang-Young Park shares his own brushing data with others. When an e-mail address of a person who is wanted to share the brushing data is input in the e-mail input field of FIG. 6A, as illustrated in FIG. 6B, a pop-up window that asks whether to accept the sharing is provided to a user who uses the corresponding e-mail. If the sharing accept is pressed, the brushing data of the user Chang-Young Park may be checked through the user's own application as illustrated in FIG. 6C.

Figure 6C:
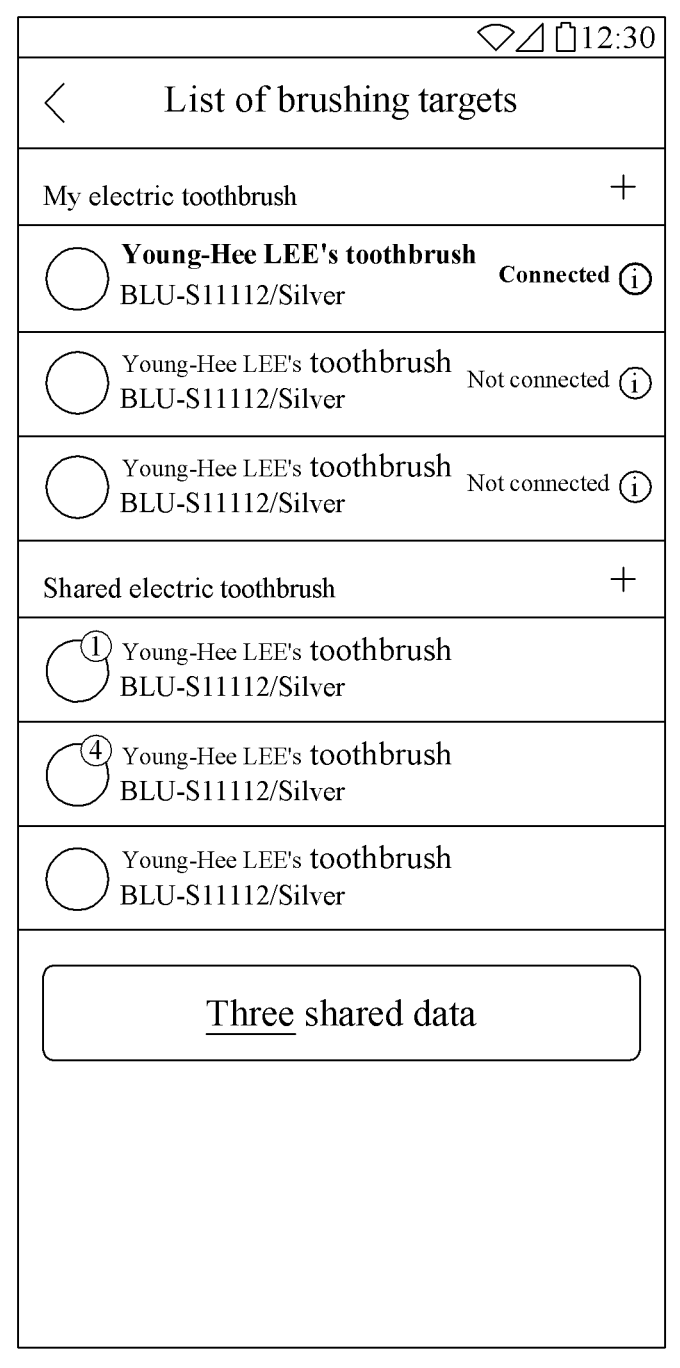
Figure 6D:
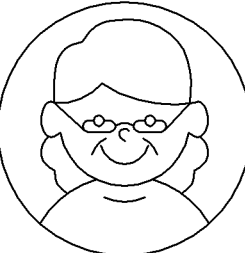

Referring to FIG. 6C, a list of the user's electric toothbrushes and a list of electric toothbrushes which are shared with the user are searched. When a specific shared electric toothbrush is selected, as illustrated in FIG. 6D, information of a user who uses the corresponding electric toothbrush may be checked. For example, information regarding a model name of an electric toothbrush which is used by the corresponding user or when the brush head is replaced may be checked. Further, when the brushing data is shared, the user who shares the brushing data brushes the teeth, a notification indicating that the user brushed the teeth may be received.

Further, the brushing data sharing function may help to provide a care service for the senior citizens who live alone. For example, when a public official in charge of caring the senior citizens who live alone in each region shares the brushing data, the public official may remotely monitor whether the senior citizens are eating well or having any health problems.

FIGS. 7A to 7F are views illustrating a user screen (GUI) of an electric toothbrush setting function of an application which is capable of being interlinked with an electric toothbrush according to an embodiment of the present invention.

Figure 7A:
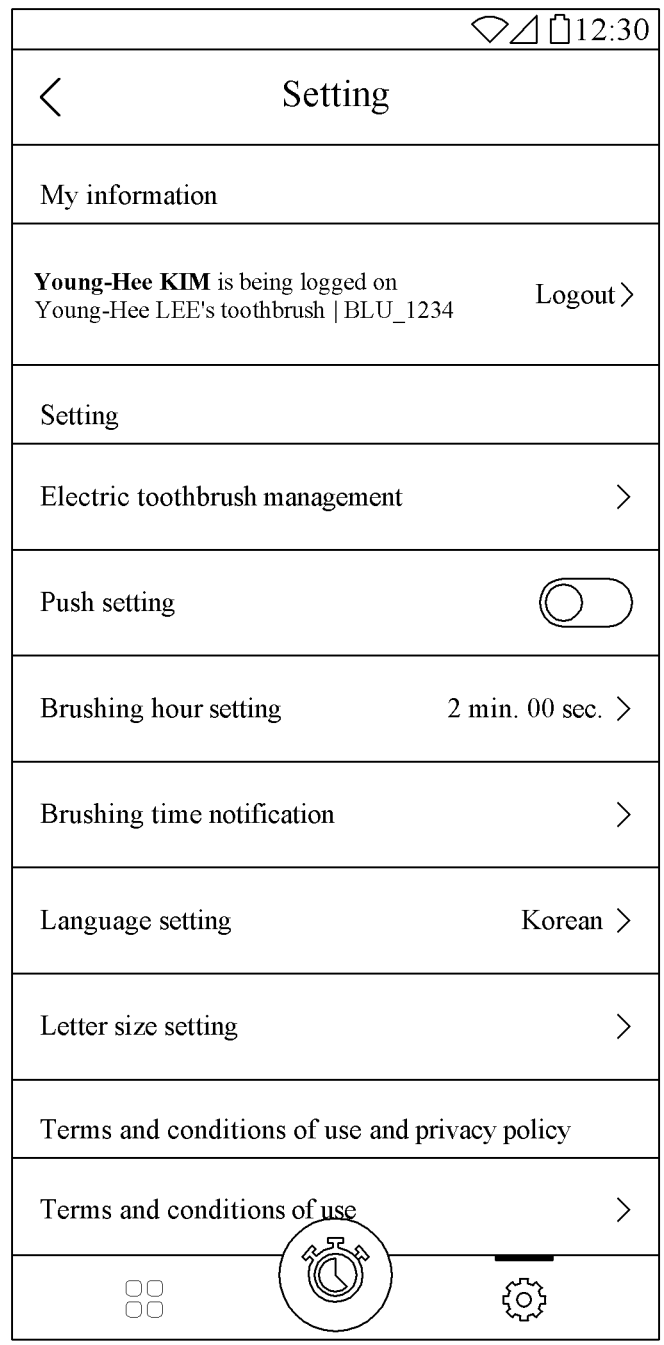
FIGS. 7A to 7F are views illustrating a user screen (GUI) of an electric toothbrush setting function of an application which is capable of being interlinked with an electric toothbrush according to an embodiment of the present invention.

The electric toothbrush setting function is a screen which expands the function of the electric toothbrush connection area 213 of FIG. 3A. Referring to FIG. 7A, it is possible to set whether to receive a push notification regarding the operation of the electric toothbrush 100, how much minutes to set a basic brushing hour, whether to receive a notification when a predetermined brushing time is reached, which time to set the brushing time.

Figure 7B:
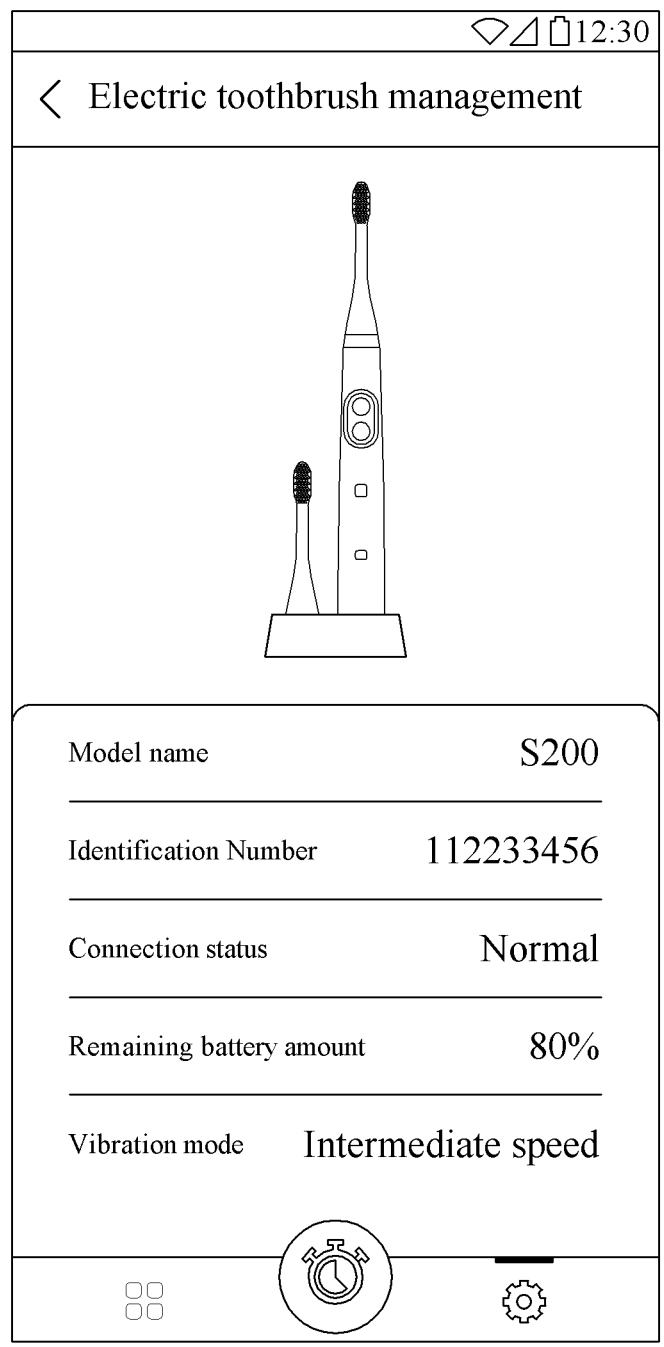

Referring to FIG. 7B, a user screen when an electric toothbrush management menu is touched in FIG. 7A is illustrated. In the screen of FIG. 7B, it is possible to set a model name of the electric toothbrush 100 connected through the Bluetooth, an identification number of the corresponding electric toothbrush, a connection status, a remaining battery amount, a vibration mode, and a brushing strength. When the application is used, even though a user is not good at using the electric toothbrush 100, the user may easily set in accordance with the user's preference through the smartphone application.

Figure 7C:
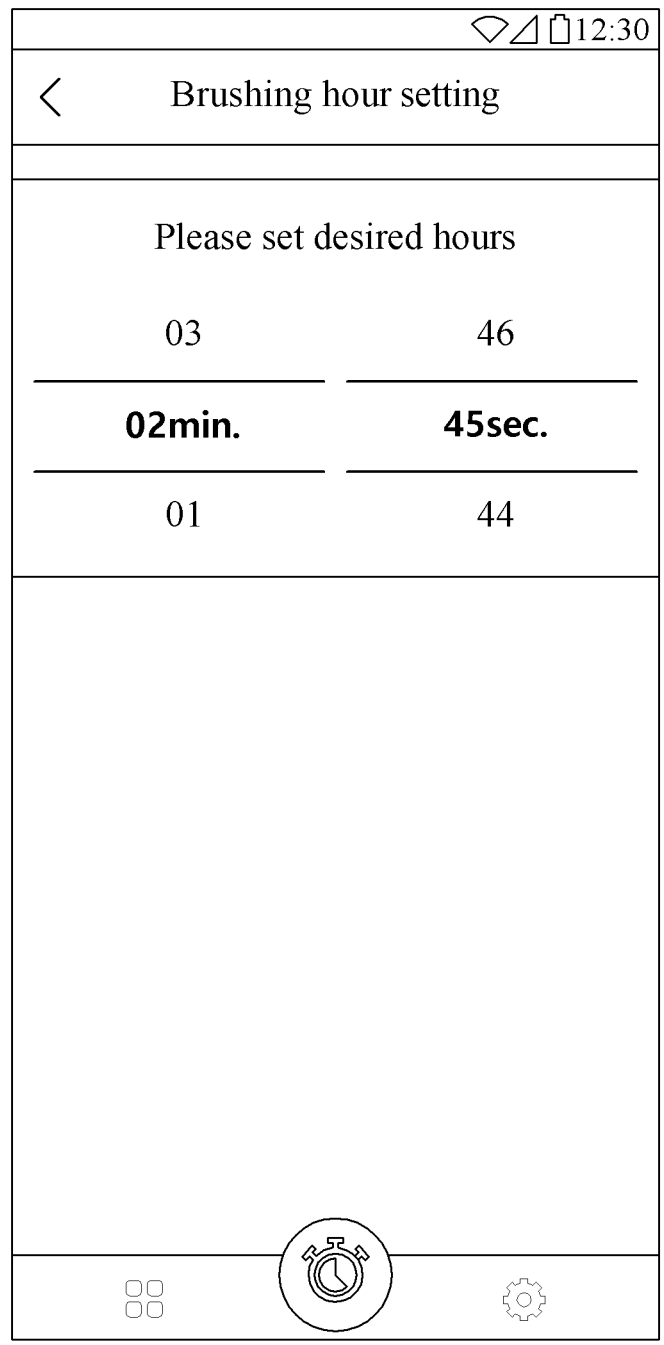

Referring to FIG. 7C, a user screen when a brushing hour setting menu is touched in FIG. 7A is illustrated. In a screen of FIG. 7C, a preferred time to brush the teeth once may be set.

Referring to FIG. 7C, it is understood that the brushing hour setting is changed from 2 minutes of FIG. 7A to 2 minutes 45 seconds.

Figure 7D:
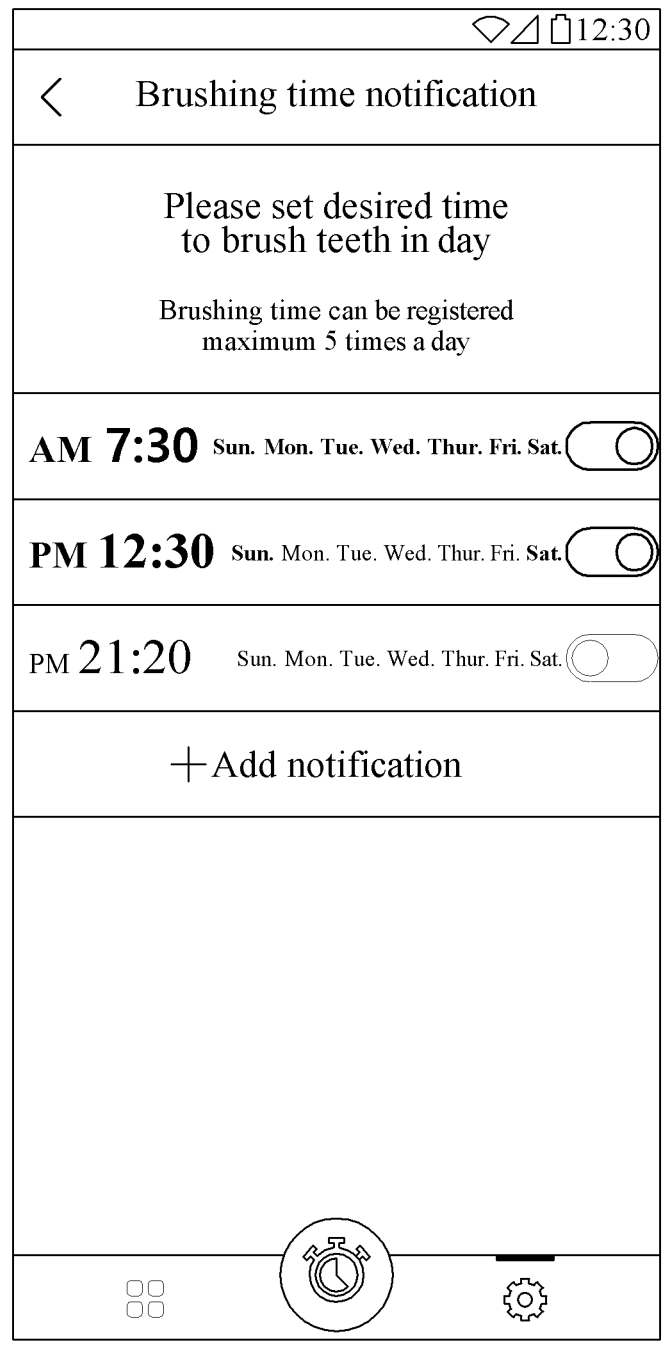

Referring to FIG. 7D, a user screen when a brushing timing notification menu is touched in FIG. 7A is illustrated. In the screen of FIG. 7D, a desired time of the day to brush the teeth may be set. Specifically, it is possible to set the morning/afternoon and hours/minutes/day of the week and also possible to set whether to issue an alarm at the corresponding timing using a toggle button.

Figure 7E:
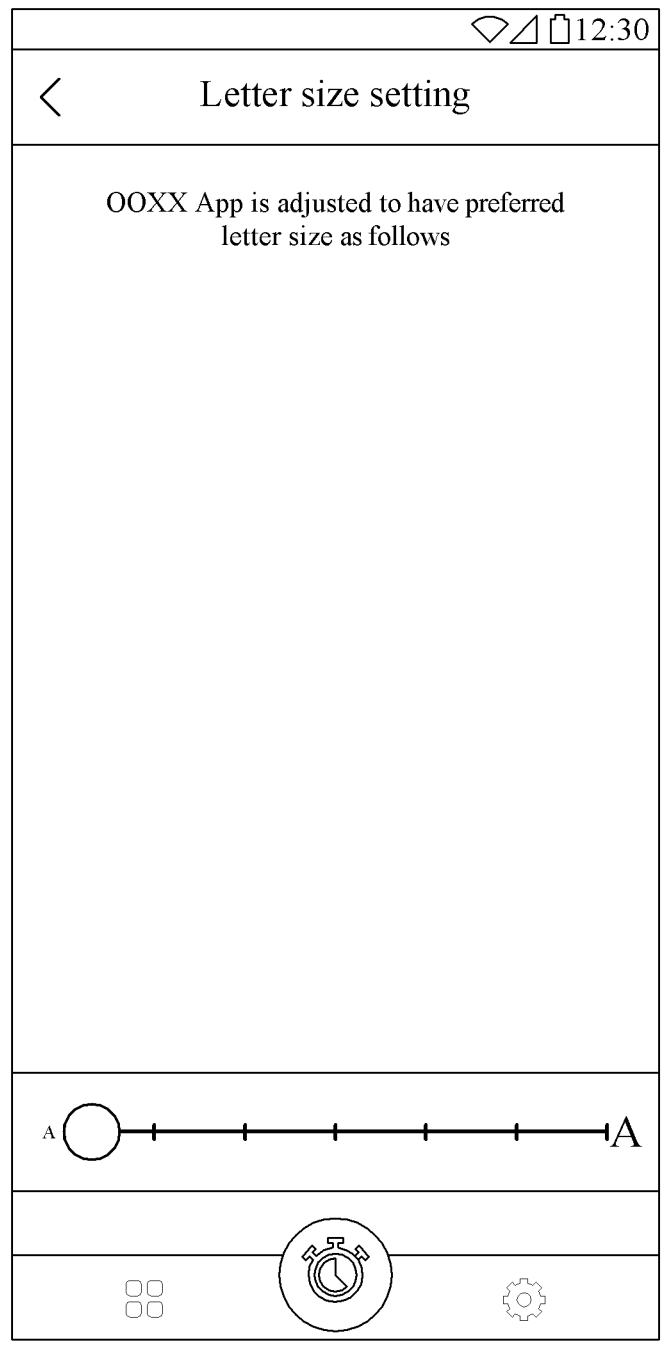
Figure 7F:
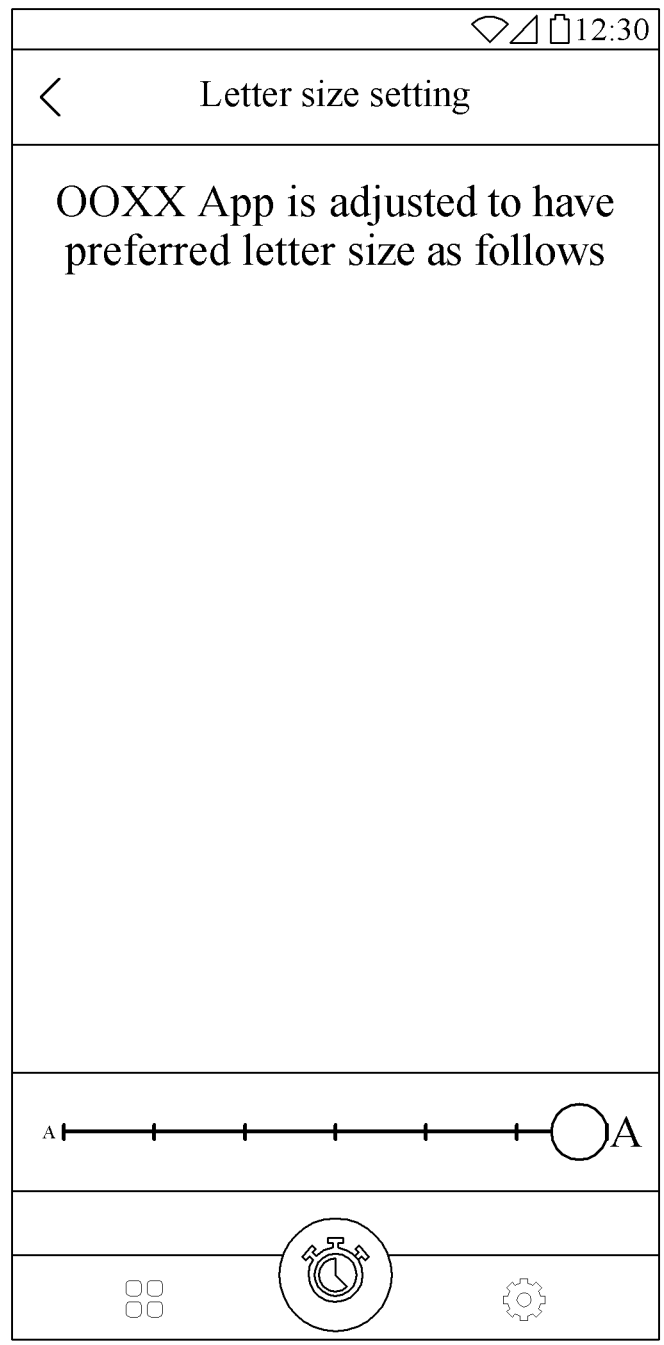

Referring to FIGS. 7E and 7F, a user screen when a letter size setting menu is touched in FIG. 7A is illustrated. FIG. 7E is a screen illustrating a letter size which is set to be the smallest. FIG. 7F is a screen illustrating a letter size which is set to be the largest. This function is provided for a user of the electric toothbrush 100 who is a senior citizen.

Figure 8:
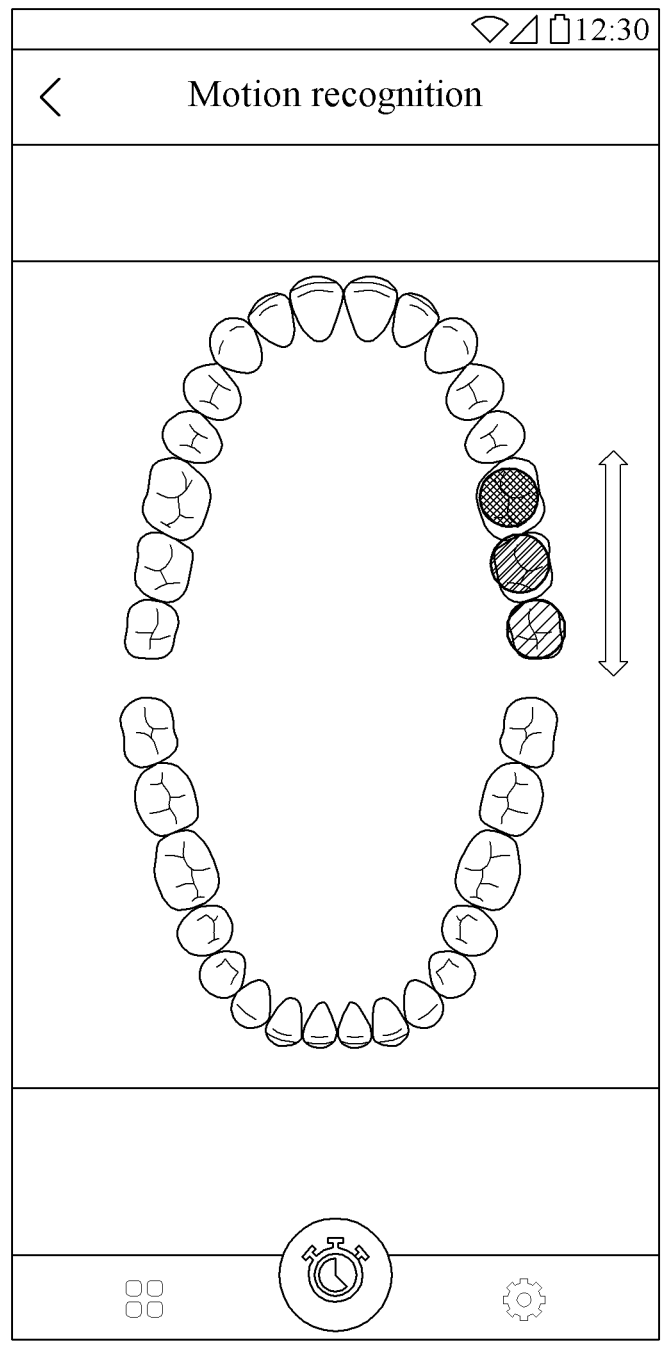
FIG. 8 is a view illustrating a user screen (GUI) of a motion recognizing function of an application which is capable of being interlinked with an electric toothbrush according to an embodiment of the present invention.

FIG. 8 is a view illustrating a user screen (GUI) of a motion recognizing function of an application which is capable of being interlinked with an electric toothbrush according to an embodiment of the present invention.

The electric toothbrush 100 of the present invention includes a 6-axis sensor to measure a gradient/rotation/speed. That is, it is possible to determine whether the brush head 110 is facing upward or downward and also possible to determine whether the electric toothbrush 100 is reciprocating forward/backward or left/right. Further, when it is input whether the user of the electric toothbrush 100 is a right-handed person or left-handed person, it is possible to determine when the user brushes right teeth or left teeth through motion recognition.

The information is collected to create and provide visual information indicating whether the user evenly brushes all the teeth through the application. Referring to FIG. 8, it is understood that the user is brushing an upper right molar with respect to the user. That is, it is analyzed that the brush head is facing upwardly and the electric toothbrush 100 is reciprocating forward/backward by the motion recognition.

By doing this, in consideration of the brushing strength, the vibration mode, and a brushing position of the electric toothbrush 100, it is possible to analyze how much every tooth has been brushed. The analyzed information as described above is visualized to be seen by the user. Referring to FIG. 8, the innermost molar is colored with blue so that it is understood that the innermost molar is sufficiently brushed. A molar next to the innermost molar is colored with green so that it is understood that the molar needs to be brushed little more. Further, another next molar is colored with orange color so that it is visualized that the molar needs to be brushed much more.

Therefore, when how much the teeth are brushed is visualized in accordance with a situation that the user brushes the teeth using the electric toothbrush 100, children who hate brushing teeth may enjoy the brushing like a game. The color changes according to how much the children brush the teeth while reciprocating the electric toothbrush 100 by themselves, so that the children may brush the teeth with interest as if they play a game. Further, a habit of evenly brushing all the teeth may be developed.

Figure 9:
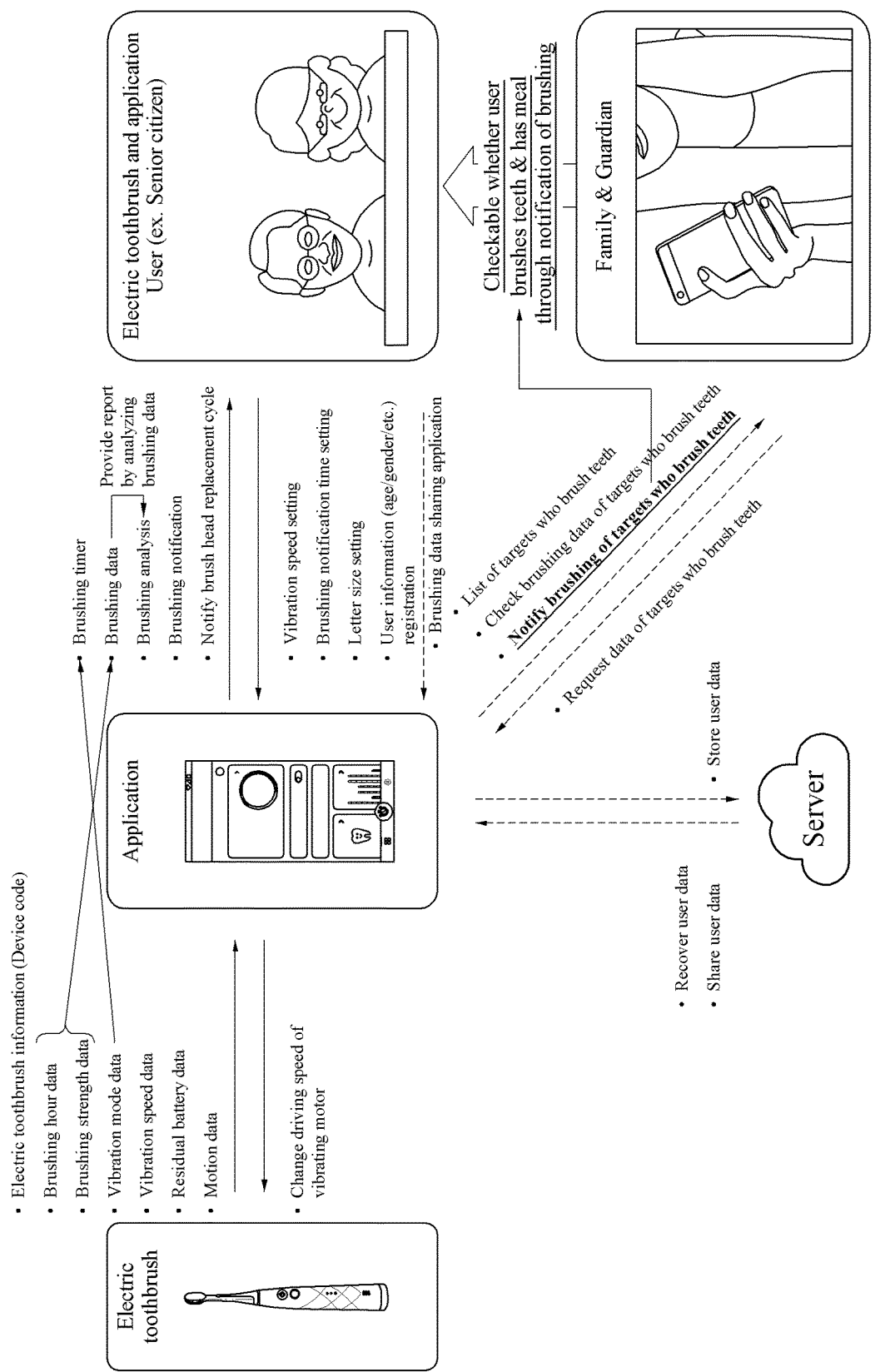
FIG. 9 is a view illustrating a flow of data among an electric toothbrush, an application, and a server according to an embodiment of the present invention.

FIG. 9 is a view illustrating a flow of data among an electric toothbrush, an application, and a server according to an embodiment of the present invention.

Referring to FIG. 9, information about the electric toothbrush, that is, a device code and brushing hour data, brushing strength data, vibration mode data, vibration speed data, remaining battery data, and motion data are transmitted from the electric toothbrush 100 to the application of the smartphone. In contrast, various setting data, for example, information for changing a driving speed of the vibrating motor is transmitted from the smartphone application to the electric toothbrush 100.

The smartphone application analyzes data collected from the electric toothbrush 100 and provides brushing data to the user. Further, the smartphone application may provide a function of changing the setting of the electric toothbrush 100 through the user screen described above. Further, the application and the server may provide a function of sharing the brushing data through the communication. Further, a recovery function of user data may also be provided.

According to this system, it is possible not only to brush teeth simply using the electric toothbrush 100, but also to analyze and evaluate data in accordance with a brushing behavior of the user by registering users for individual electric toothbrushes through an application, to systematically manage the oral care.

It will be appreciated that various exemplary embodiments of the present invention have been described herein for purposes of illustration, and that various modifications, changes, and substitutions may be made by those skilled in the art without departing from the scope and spirit of the present invention. Therefore, the exemplary embodiments of the present disclosure are provided for illustrative purposes only but not intended to limit the technical concept of the present disclosure. The scope of the technical concept of the present disclosure is not limited thereto. The protective scope of the present disclosure should be construed based on the following claims, and all the technical concepts in the equivalent scope thereof should be construed as falling within the scope of the present disclosure.

The invention claimed is:

1. An oral care method using an electric toothbrush, the method comprising:
   receiving brushing data from an electric toothbrush, by an application; and
   displaying a brushing score indicating how much a brushing is performed by analyzing the brushing data by the application,
   wherein the displaying the brushing score comprises:
   calculating the brushing score by the following Equation:

$$\text{Brushing score} = \text{Number of brushing times} * A + \text{Brushing hour (s)} * B - \text{Score of brushing strength}, \quad \text{[Equation]}$$

where A and B are constants and a score of the brushing strength is a value obtained by converting a pressure when the brushing is performed into a predetermined value.

2. The oral care method using an electric toothbrush of claim 1, wherein the receiving the brushing data comprises:
   receiving on-time and off-time data from the electric toothbrush and calculating a difference therebetween into a brushing hour.

3. The oral care method using an electric toothbrush of claim 1, wherein the displaying the brushing score comprises:
   displaying values obtained by cumulatively adding the brushing scores on a daily basis together with daily statistic data for each day on a weekly basis.

4. The oral care method using an electric toothbrush of claim 1, wherein the displaying the brushing score comprises:
   displaying values obtained by cumulatively adding the brushing scores on a daily basis together with data obtained by visualizing the brushing score for each day on a monthly basis.

5. The oral care method using an electric toothbrush of claim 1, further comprising:
   sharing the brushing score with an application of another device.

6. The oral care method using an electric toothbrush of claim 1, further comprising:
   receiving an input regarding a setting of the electric toothbrush from a user, by the application; and
   transmitting a control signal of the electric toothbrush in accordance with the input to the electric toothbrush, by the application.

7. An oral care method using an electric toothbrush, the method comprising:
   receiving brushing data from an electric toothbrush, by an application;

displaying a brushing score indicating how much a brushing is performed by analyzing the brushing data by the application;

receiving a current consumption measurement value of a vibrating motor from the electric toothbrush, by the application; and determining a brushing strength by comparing the current consumption measurement value with a predetermined optimal current value, by the application.

8. The oral care method using an electric toothbrush of claim 1, wherein the receiving the brushing data comprises:

receiving the brushing data in real time, and wherein the displaying the brushing score comprises:

analyzing a direction of a brush head of the electric toothbrush and a direction of a reciprocating motion for brushing to determine a tooth which is being brushed and a progressive degree of the brushing and displaying the determined result to a user in real time.

* * * * *